(12) United States Patent
Baek et al.

(10) Patent No.: US 12,098,174 B2
(45) Date of Patent: Sep. 24, 2024

(54) OCT-3/4 VARIANT

(71) Applicant: CHA UNIVERSITY INDUSTRY-ACADEMIC COOPERATION FOUNDATION, Pocheon-si (KR)

(72) Inventors: Kwang-Hyun Baek, Seoul (KR); Ji-Hye Choi, Gwangmyeong-si (KR)

(73) Assignee: CHA UNIVERSITY INDUSTRY-ACADEMIC COOPERATION FOUNDATION, Pocheon-si (KR)

( * ) Notice: Subject to any disclaimer, the term of this patent is extended or adjusted under 35 U.S.C. 154(b) by 560 days.

(21) Appl. No.: 17/310,517

(22) PCT Filed: Feb. 6, 2020

(86) PCT No.: PCT/KR2020/001678
§ 371 (c)(1),
(2) Date: Aug. 6, 2021

(87) PCT Pub. No.: WO2020/162684
PCT Pub. Date: Aug. 13, 2020

(65) Prior Publication Data
US 2022/0194998 A1 Jun. 23, 2022

(30) Foreign Application Priority Data
Feb. 7, 2019 (KR) .................. 10-2019-0014304

(51) Int. Cl.
*C07K 14/47* (2006.01)
(52) U.S. Cl.
CPC ................. *C07K 14/4702* (2013.01)
(58) Field of Classification Search
CPC ................................ C07K 14/4702
See application file for complete search history.

(56) References Cited

FOREIGN PATENT DOCUMENTS

KR 10-2018-0121046 A 11/2018

OTHER PUBLICATIONS

Human Oct4 Sequence, from https://www.uniprot.org/uniprotkb/Q01860/entry, 1993, pp. 1-12.*
Xu et al., Proteomic identification of protein ubiquitination events, Biotechnology and Genetic Engineering Reviews, 2013, 29, pp. 73-109.*
Terpe, Overview of tag protein fusions: from molecular and biochemical fundamentals to commercial systems, Appl Microbiol Biotechnol, 2003, 60, pp. 523-533.*
Choi et al., "Cellular functions of stem cell factors mediated by the ubiquitin-proteasome system", Cell. Mol. Life Sci., 2018, vol. 75, pp. 1947-1957.
Li et al., "Disruption of OCT4 Ubiquitination Increases OCT4 Protein Stability and ASH2L-B-Mediated H3K4 Methylation Promoting Pluripotency Acquisition", Stem Cell Reports, 2018, vol. 11, pp. 973-987.
Naujokat et al., "Concise Review: Role and Function of the Ubiquitin-Proteasome System in Mammalian Stem and Progenitor Cells", Stem Cells, 2007, vol. 25, pp. 2408-2418.
Zhao et al., POU domain transcription factor OCT4 [*Homo sapiens*], NCBI, GenBank accession No. ADE48540.1, (2010), 2 pages.
Pan et al., "Site-specific Disruption of the Oct4/Sox2 Protein Interaction Reveals Coordinated Mesendodermal Differentiation and the Epithelial-Mesenchymal Transition", The Journal of Biological Chemistry, 2016, vol. 291, No. 35, pp. 18353-18369.
Ring et al., "Direct Reprogramming of Mouse and Human Fibroblasts into Multipotent Neural Stem Cells with a Single Factor", Cell Stem Cell., 2012, vol. 11, No. 1, pp. 100-109.
Takahashi et al., "Induction of Pluripotent Stem Cells from Mouse Embryonic and Adult Fibroblast Cultures by Defined Factors", Cell, 2006, vol. 126, pp. 663-676.
Villodre et al., "Roles of OCT4 in tumorigenesis, cancer therapy resistance and prognosis", Cancer Treatment Reviews, 2016, vol. 51, pp. 1-9.
Yu et al., "Induced Pluripotent Stem Cell Lines Derived from Human Somatic Cells", Science, 2007, vol. 318, pp. 1917-1920.
Zhang et al., "Post-translational modification of POU domain transcription factor Oct-4 by SUMO-1", FASEB J., 2007, vol. 21, pp. 3042-3051.

* cited by examiner

*Primary Examiner* — Li N Komatsu
(74) *Attorney, Agent, or Firm* — Vorys, Sater, Seymour and Pease LLP; Mih Suhn Koh (57) ABSTRACT

The present invention provides an Oct-3/4 protein variant wherein lysine at position 156; lysine at position 286; or lysines at positions 156 and 286 in the Oct-3/4 protein is (are) substituted with arginine. The Oct-3/4 protein variant according to the present invention can inhibit a protein degradation mechanism through ubiquitination, and shows a higher half-life, compared to the wild-type Oct-3/4, thereby exhibiting high stability.

3 Claims, 3 Drawing Sheets
Specification includes a Sequence Listing.

SEQUENCE LISTING

<160> NUMBER OF SEQ ID NOS: 13

<210> SEQ ID NO 1
<211> LENGTH: 360
<212> TYPE: PRT
<213> ORGANISM: Homo sapiens

<400> SEQUENCE: 1

Met Ala Gly His Leu Ala Ser Asp Phe Ala Phe Ser Pro Pro Pro Gly
1               5                   10                  15

Gly Gly Gly Asp Gly Pro Gly Gly Pro Glu Pro Gly Trp Val Asp Pro
            20                  25                  30

-continued

```
Arg Thr Trp Leu Ser Phe Gln Gly Pro Pro Gly Pro Gly Ile Gly
         35                  40                  45
Pro Gly Val Gly Pro Gly Ser Glu Val Trp Gly Ile Pro Pro Cys Pro
 50                  55                  60
Pro Pro Tyr Glu Phe Cys Gly Gly Met Ala Tyr Cys Gly Pro Gln Val
 65                  70                  75                  80
Gly Val Gly Leu Val Pro Gln Gly Gly Leu Glu Thr Ser Gln Pro Glu
                 85                  90                  95
Gly Glu Ala Gly Val Gly Val Glu Ser Asn Ser Asp Gly Ala Ser Pro
             100                 105                 110
Glu Pro Cys Thr Val Thr Pro Gly Ala Val Lys Leu Glu Lys Glu Lys
         115                 120                 125
Leu Glu Gln Asn Pro Glu Glu Ser Gln Asp Ile Lys Ala Leu Gln Lys
 130                 135                 140
Glu Leu Glu Gln Phe Ala Lys Leu Leu Lys Gln Lys Arg Ile Thr Leu
145                 150                 155                 160
Gly Tyr Thr Gln Ala Asp Val Gly Leu Thr Leu Gly Val Leu Phe Gly
                165                 170                 175
Lys Val Phe Ser Gln Thr Thr Ile Cys Arg Phe Glu Ala Leu Gln Leu
            180                 185                 190
Ser Phe Lys Asn Met Cys Lys Leu Arg Pro Leu Leu Gln Lys Trp Val
        195                 200                 205
Glu Glu Ala Asp Asn Asn Glu Asn Leu Gln Glu Ile Cys Lys Ala Glu
 210                 215                 220
Thr Leu Val Gln Ala Arg Lys Arg Lys Arg Thr Ser Ile Glu Asn Arg
225                 230                 235                 240
Val Arg Gly Asn Leu Glu Asn Leu Phe Leu Gln Cys Pro Lys Pro Thr
                245                 250                 255
Leu Gln Gln Ile Ser His Ile Ala Gln Gln Leu Gly Leu Glu Lys Asp
            260                 265                 270
Val Val Arg Val Trp Phe Cys Asn Arg Arg Gln Lys Gly Lys Arg Ser
        275                 280                 285
Ser Ser Asp Tyr Ala Gln Arg Glu Asp Phe Glu Ala Ala Gly Ser Pro
 290                 295                 300
Phe Ser Gly Gly Pro Val Ser Phe Pro Leu Ala Pro Gly Pro His Phe
305                 310                 315                 320
Gly Thr Pro Gly Tyr Gly Ser Pro His Phe Thr Ala Leu Tyr Ser Ser
                325                 330                 335
Val Pro Phe Pro Glu Gly Glu Ala Phe Pro Pro Val Ser Val Thr Thr
            340                 345                 350
Leu Gly Ser Pro Met His Ser Asn
        355                 360

<210> SEQ ID NO 2
<211> LENGTH: 2300
<212> TYPE: DNA
<213> ORGANISM: Homo sapiens

<400> SEQUENCE: 2
ggaaaaaagg aaagtgcact tggaagagat ccaagtgggc aacttgaaga acaagtgcca      60
aatagcactt ctgtcatgct ggatgtcagg gctctttgtc cactttgtat agccgctggc     120
ttatagaagg tgctcgataa atctcttgaa tttaaaaatc aattaggatg cctctatagt     180 gaaaagata  cagtaaagat gagggataat caatttaaaa aatgagtaag tacacacaaa     240
```

```
gcactttatc cattcttatg acacctgtta cttttttgct gtgtttgtgt gtatgcatgc    300
catgttatag tttgtgggac cctcaaagca agctggggag agtatatact gaatttagct    360
tctgagacat gatgctcttc cttttaatt aacccagaac ttagcagctt atctatttct     420
ctaatctcaa aacatcctta aactgggggt gatacttgag tgagagaatt ttgcaggtat    480
taaatgaact atcttctttt tttttttct ttgagacaga gtcttgctct gtcacccagg     540
ctggagtgca gtggcgtgat ctcagctcac tgcaacctcc gcctcccggg ttcaagtgat    600
tctcctgcct cagcctcctg agtagctggg attacaggtg cgtgccaccg tgcccagcta    660
atttttgtgt tttagtaga  gacggggttt caccatgttg gccatgctgg tcttgaactc    720
ctgacctcgt gatctgccca cctcggcctc ccaaagtgct ggaattatag gcgtgagcca    780
ccgcgcccag caagaacttt ctaaccttca aacctgaca  ggtgttctcg aggccagggt    840
ctctctttct gtcctttcac gatgctctgc atcccttgga tgtgccagtt tctggggaa    900 gagtagtcct ttgttacatg catgagtcag tgaacaggga atgggtgaat gacatttgtg   960
ggtaggttat ttctagaagt taggtgggca gcttggaagg cagaggcact tctacagact   1020
attccttggg gccacacgta ggttcttgaa tcccgaatgg aaaggggaga ttgataactg   1080
gtgtgtttat gttcttacaa gtcttctgcc ttttaaaatc cagtcccagg acatcaaagc   1140
tctgcagaaa gaactcgagc aatttgccaa gctcctgaag cagaagagga tcaccctggg   1200
atatacacag gccgatgtgg ggctcaccct gggggttcta tttggtgggt tccctctgc    1260 agattctgac cgcatctccc ctctaaggag tatccctgaa cctagtgggg aggggcaggg   1320
gcagactacc ctcacccatg aagaggagta gggagaggga gaagatgctt tgagctccct   1380 ctggaagag  gtggtaagct tggatctcag ggtcacaagg gccctgcgtg ctccctcact   1440
ttgcttctct tttgactggc ctcccccagg gaaggtattc agccaaacga ccatctgccg   1500
ctttgaggct ctgcagctta gcttcaagaa catgtgtaag ctgcggccct tgctgcagaa   1560
gtgggtggag gaagctgaca acaatgaaaa tcttcaggag atatgcaaag cagaaaccct   1620
cgtgcaggcc cgaaagagaa agcgaaccag tatcgagaac cgagtgagag gcaacctgga   1680
gaatttgttc ctgcagtgcc cgaaacccac actgcagcag atcagccaca tcgcccagca   1740
gcttgggctc gagaaggatg tggtccgagt gtggttctgt aaccggcgcc agaagggcaa   1800
gcgatcaagc agcgactatg cacaacgaga ggattttgag gctgctgggt ctccttttctc  1860 aggggggacca gtgtcctttc ctctggcccc agggccccat tttggtaccc caggctatgg   1920
gagccctcac ttcactgcac tgtactcctc ggtccctttc cctgagggg  aagccttcc    1980 ccctgtctcc gtcaccactc tgggctctcc catgcattca aactgaggtg cctgcccttc   2040
taggaatggg ggacaggggg aggggaggag ctagggaaaa aaaacctgga gtttgtgcca   2100 gggttttttgg gattaagttc ttcattcact aaggaaggaa ttgggaacac aaagggtggg   2160
ggcaggggag tttggggcaa ctggttggag ggaaggtgaa gttcaatgat gctcttgatt   2220
ttaatcccac atcatgtatc acttttttct taaataaaga agcctgggac acagtagata   2280
gacacactta aaaaaaaaaa                                               2300
```

<210> SEQ ID NO 3
<211> LENGTH: 360
<212> TYPE: PRT
<213> ORGANISM: Artificial Sequence
<220> FEATURE:
<223> OTHER INFORMATION: Mutant -continued

<400> SEQUENCE: 3

```
Met Ala Gly His Leu Ala Ser Asp Phe Ala Phe Ser Pro Pro Gly
1               5                   10                  15

Gly Gly Gly Asp Gly Pro Gly Pro Glu Pro Gly Trp Val Asp Pro
            20                  25                  30

Arg Thr Trp Leu Ser Phe Gln Gly Pro Pro Gly Pro Gly Ile Gly
            35                  40                  45

Pro Gly Val Gly Pro Gly Ser Glu Val Trp Gly Ile Pro Pro Cys Pro
        50                  55                  60

Pro Pro Tyr Glu Phe Cys Gly Gly Met Ala Tyr Cys Gly Pro Gln Val
65              70                  75                  80

Gly Val Gly Leu Val Pro Gln Gly Gly Leu Glu Thr Ser Gln Pro Glu
                85                  90                  95

Gly Glu Ala Gly Val Gly Val Ser Asn Ser Asp Gly Ala Ser Pro
            100                 105                 110

Glu Pro Cys Thr Val Thr Pro Gly Ala Val Lys Leu Glu Lys Glu Lys
                115                 120                 125

Leu Glu Gln Asn Pro Glu Ser Gln Asp Ile Lys Ala Leu Gln Lys
130                 135                 140

Glu Leu Glu Gln Phe Ala Lys Leu Leu Lys Gln Arg Arg Ile Thr Leu
145                 150                 155                 160

Gly Tyr Thr Gln Ala Asp Val Gly Leu Thr Leu Gly Val Leu Phe Gly
                165                 170                 175

Lys Val Phe Ser Gln Thr Thr Ile Cys Arg Phe Glu Ala Leu Gln Leu
                180                 185                 190

Ser Phe Lys Asn Met Cys Lys Leu Arg Pro Leu Leu Gln Lys Trp Val
            195                 200                 205

Glu Glu Ala Asp Asn Asn Glu Asn Leu Gln Glu Ile Cys Lys Ala Glu
210                 215                 220

Thr Leu Val Gln Ala Arg Lys Arg Lys Arg Thr Ser Ile Glu Asn Arg
225                 230                 235                 240

Val Arg Gly Asn Leu Glu Asn Leu Phe Leu Gln Cys Pro Lys Pro Thr
                245                 250                 255

Leu Gln Gln Ile Ser His Ile Ala Gln Gln Leu Gly Leu Glu Lys Asp
            260                 265                 270

Val Val Arg Val Trp Phe Cys Asn Arg Arg Gln Lys Gly Lys Arg Ser
        275                 280                 285

Ser Ser Asp Tyr Ala Gln Arg Glu Asp Phe Glu Ala Ala Gly Ser Pro
290                 295                 300

Phe Ser Gly Gly Pro Val Ser Phe Pro Leu Ala Pro Gly Pro His Phe
305                 310                 315                 320

Gly Thr Pro Gly Tyr Gly Ser Pro His Phe Thr Ala Leu Tyr Ser Ser
                325                 330                 335

Val Pro Phe Pro Glu Gly Glu Ala Phe Pro Pro Val Ser Val Thr Thr
                340                 345                 350

Leu Gly Ser Pro Met His Ser Asn
                355                 360
```

<210> SEQ ID NO 4
<211> LENGTH: 360
<212> TYPE: PRT
<213> ORGANISM: Artificial Sequence
<220> FEATURE:
<223> OTHER INFORMATION: Mutant

<400> SEQUENCE: 4

```
Met Ala Gly His Leu Ala Ser Asp Phe Ala Phe Ser Pro Pro Pro Gly
1               5                   10                  15
Gly Gly Gly Asp Gly Pro Gly Pro Glu Pro Gly Trp Val Asp Pro
            20                  25                  30
Arg Thr Trp Leu Ser Phe Gln Gly Pro Pro Gly Pro Gly Ile Gly
            35                  40                  45
Pro Gly Val Gly Pro Gly Ser Glu Val Trp Gly Ile Pro Pro Cys Pro
    50                  55                  60
Pro Pro Tyr Glu Phe Cys Gly Gly Met Ala Tyr Cys Gly Pro Gln Val
65                  70                  75                  80
Gly Val Gly Leu Val Pro Gln Gly Gly Leu Glu Thr Ser Gln Pro Glu
            85                  90                  95
Gly Glu Ala Gly Val Gly Val Ser Asn Ser Asp Gly Ala Ser Pro
            100                 105                 110
Glu Pro Cys Thr Val Thr Pro Gly Ala Val Lys Leu Glu Lys Glu Lys
            115                 120                 125
Leu Glu Gln Asn Pro Glu Glu Ser Gln Asp Ile Lys Ala Leu Gln Lys
    130                 135                 140
Glu Leu Glu Gln Phe Ala Lys Leu Leu Lys Gln Lys Arg Ile Thr Leu
145                 150                 155                 160
Gly Tyr Thr Gln Ala Asp Val Gly Leu Thr Leu Gly Val Leu Phe Gly
            165                 170                 175
Lys Val Phe Ser Gln Thr Thr Ile Cys Arg Phe Glu Ala Leu Gln Leu
            180                 185                 190
Ser Phe Lys Asn Met Cys Lys Leu Arg Pro Leu Leu Gln Lys Trp Val
    195                 200                 205
Glu Glu Ala Asp Asn Asn Glu Asn Leu Gln Glu Ile Cys Lys Ala Glu
210                 215                 220
Thr Leu Val Gln Ala Arg Lys Arg Lys Arg Thr Ser Ile Glu Asn Arg
225                 230                 235                 240
Val Arg Gly Asn Leu Glu Asn Leu Phe Leu Gln Cys Pro Lys Pro Thr
            245                 250                 255
Leu Gln Gln Ile Ser His Ile Ala Gln Gln Leu Gly Leu Glu Lys Asp
            260                 265                 270
Val Val Arg Val Trp Phe Cys Asn Arg Arg Gln Lys Gly Arg Arg Ser
    275                 280                 285
Ser Ser Asp Tyr Ala Gln Arg Glu Asp Phe Glu Ala Ala Gly Ser Pro
290                 295                 300
Phe Ser Gly Gly Pro Val Ser Phe Pro Leu Ala Pro Gly Pro His Phe
305                 310                 315                 320
Gly Thr Pro Gly Tyr Gly Ser Pro His Phe Thr Ala Leu Tyr Ser Ser
            325                 330                 335
Val Pro Phe Pro Glu Gly Glu Ala Phe Pro Pro Val Ser Val Thr Thr
            340                 345                 350
Leu Gly Ser Pro Met His Ser Asn
355                 360
```

<210> SEQ ID NO 5
<211> LENGTH: 360
<212> TYPE: PRT
<213> ORGANISM: Artificial Sequence
<220> FEATURE:
<223> OTHER INFORMATION: Mutant

<400> SEQUENCE: 5

```
Met Ala Gly His Leu Ala Ser Asp Phe Ala Phe Ser Pro Pro Gly
1               5                   10                  15

Gly Gly Gly Asp Gly Pro Gly Pro Glu Pro Gly Trp Val Asp Pro
            20                  25                  30

Arg Thr Trp Leu Ser Phe Gln Gly Pro Pro Gly Pro Gly Ile Gly
        35                  40                  45

Pro Gly Val Gly Pro Gly Ser Glu Val Trp Gly Ile Pro Pro Cys Pro
    50                  55                  60

Pro Pro Tyr Glu Phe Cys Gly Gly Met Ala Tyr Cys Gly Pro Gln Val
65              70                  75                  80

Gly Val Gly Leu Val Pro Gln Gly Gly Leu Glu Thr Ser Gln Pro Glu
                85                  90                  95

Gly Glu Ala Gly Val Gly Val Ser Asn Ser Asp Gly Ala Ser Pro
                100                 105                 110

Glu Pro Cys Thr Val Thr Pro Gly Ala Val Lys Leu Glu Lys Glu Lys
            115                 120                 125

Leu Glu Gln Asn Pro Glu Ser Gln Asp Ile Lys Ala Leu Gln Lys
    130                 135                 140

Glu Leu Glu Gln Phe Ala Lys Leu Leu Lys Gln Arg Arg Ile Thr Leu
145                 150                 155                 160

Gly Tyr Thr Gln Ala Asp Val Gly Leu Thr Leu Gly Val Leu Phe Gly
                165                 170                 175

Lys Val Phe Ser Gln Thr Thr Ile Cys Arg Phe Glu Ala Leu Gln Leu
                180                 185                 190

Ser Phe Lys Asn Met Cys Lys Leu Arg Pro Leu Leu Gln Lys Trp Val
    195                 200                 205

Glu Glu Ala Asp Asn Asn Glu Asn Leu Gln Glu Ile Cys Lys Ala Glu
210                 215                 220

Thr Leu Val Gln Ala Arg Lys Arg Lys Arg Thr Ser Ile Glu Asn Arg
225                 230                 235                 240

Val Arg Gly Asn Leu Glu Asn Leu Phe Leu Gln Cys Pro Lys Pro Thr
                245                 250                 255

Leu Gln Gln Ile Ser His Ile Ala Gln Gln Leu Gly Leu Glu Lys Asp
    260                 265                 270

Val Val Arg Val Trp Phe Cys Asn Arg Arg Gln Lys Gly Arg Arg Ser
    275                 280                 285

Ser Ser Asp Tyr Ala Gln Arg Glu Asp Phe Glu Ala Ala Gly Ser Pro
290                 295                 300

Phe Ser Gly Gly Pro Val Ser Phe Pro Leu Ala Pro Gly Pro His Phe
305                 310                 315                 320

Gly Thr Pro Gly Tyr Gly Ser Pro His Phe Thr Ala Leu Tyr Ser Ser
                325                 330                 335

Val Pro Phe Pro Glu Gly Glu Ala Phe Pro Pro Val Ser Val Thr Thr
            340                 345                 350

Leu Gly Ser Pro Met His Ser Asn
            355                 360
```

<210> SEQ ID NO 6
<211> LENGTH: 21
<212> TYPE: DNA
<213> ORGANISM: Artificial Sequence
<220> FEATURE:
<223> OTHER INFORMATION: Primer -continued

```
<400> SEQUENCE: 6
gagaaggaga ggctggagca a                                       21

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
ttgctccagc ctctccttct c                                       21

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
gctctgcaga gagaactcga g                                       21

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
ctcgagttct ctctgcagag c                                       21

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
ctgaagcaga ggaggatcac c                                       21

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
ggtgatcctc ctctgcttca g                                       21

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
cagaagggca ggcgatcaag c                                       21

<210> SEQ ID NO 13
<211> LENGTH: 21
```

```
<212> TYPE: DNA
<213> ORGANISM: Artificial Sequence
<220> FEATURE:
<223> OTHER INFORMATION: Primer

<400> SEQUENCE: 13
gcttgatcgc ctgcccttct g                                         21
```

OCT-3/4 VARIANT

SEQUENCE LISTING

The Sequence Listing submitted in text format (.txt) filed on Aug. 6, 2021, named "SequenceListing.txt", created on Aug. 6, 2021 (16.1 KB), is incorporated herein by reference.

TECHNICAL FIELD

The present invention relates to variants of the Oct-3/4 protein. More specifically, the present invention relates to an Oct-3/4 protein variant in which a lysine residue(s) at a specific position(s) of the Oct-3/4 protein is (are) substituted with arginine.

BACKGROUND ART

Oct-3/4, one of the proteinaceous transcription factors that regulate gene activity, allows stem cells to maintain the ability for forming tissues of the body. In addition, the Oct-3/4 protein acts specifically on stem cells to serve as an initiator of genes for general or specific differentiation of cells. In 2007, Yamanaka' and research teams prepared induced pluripotent stem cells using Oct-3/4 as a reprogramming factor and thus revealed that Oct-3/4 is a key factor in reprogramming into induced pluripotent stem cells (Takahashi, K., & Yamanaka, S. (2006). Cell, 126(4), 663-676). (Yu, J., Vodyanik, M. A., Smuga-Otto, K., Antosiewicz-Bourget, J., Frane, J. L., Tian, S., Nie, J., Jonsdottir, G. A., Ruotti, V., Stewart, R., Slukvin, I I., & Thomson, J. A. (2007). Science, 318(5858), 1917-1920). Induced pluripotent stem cells (iPSCs), which are able to differentiate into various tissues of the body, are one of the fields actively researched worldwide; and are expected that it will play an important role in the development of cell transformation technology in the future. However, the methods for preparing and maintaining induced pluripotent stem cells are quite difficult and the development of technology for sustaining pluripotency is a field that many researchers are currently challenging.

It is being gradually reported that major proteins involved in proliferation and differentiation of cells are regulated by the ubiquitin-proteasome pathway (UPP), and thus the importance of proteolysis studies is increasing. Most proteins in cells are labeled with ubiquitin to maintain protein homeostasis through the UPP. It has been variously reported that abnormalities in this mechanism are closely related to various diseases such as cancer (Naujokat, C., & Saric, T. (2007). *Stem Cells,* 25(10), 2408-2418). Researchers are increasingly interested in how the characteristics of stem cells affect the initiation and progression of cancer, through reprogramming somatic cells to an embryonic stem cell-like state by introducing stem cell factors thereto. For example, since Oct-3/4 has been reported to show abnormal expression in cancer, researches using the stem cell regulators, for cancer research and as a therapeutic target, are increasing. Oct-3/4 is an important regulator determining the cell fate in both embryonic stem cells and cancer stem cells. If Oct-3/4 is activated at an inappropriate timing, cells are more likely to become cancer stem cells rather than normal stem cells. Indeed, there is a number of literatures reporting that the expression of Oct-3/4 is significantly correlated with the survival rate of patients with various types of cancer (Villodre, E. S., Kipper, F. C., Pereira, M. B., & Lenz, G., (2016). *Cancer Treat Rev,* 51, 1-9). In addition, in order to develop therapeutic agents for various diseases such as cancer, many studies using the proteins that regulate cellular mechanisms through various intracellular signaling pathways are being conducted (Ring, K. L., Tong, L. M., Balestra, M. E., Javier, R., Andrews-Zwilling, Y., Li, G., Walker, D., Zhang, W. R., Kreitzer, A. C., & Huang, Y. (2012). *Cell Stem Cell,* 11(1), 100-109).

Recently, the present inventors, including some research teams, have identified that homeostasis of the important proteins related to proliferation and differentiation is regulated by UPP (Choi, J., & Baek, K. H. (2017). *Cell Mol Life Sci,* 2017, 75: 1947-1957). Since the ubiquitin proteasome mechanism in cells is regulated by many proteins, it is expected that the identification of the proteins involved in cell growth and the modulation of inhibiting or inducing their degradation mechanisms make it possible to control the proliferation and differentiation of cells, thereby being able to develop function-enhanced and advanced cell therapies against diseases such as cancer. In case of Oct-3/4, the expression thereof starts in the early stage of the blastomere and then gradually decreases during the trophoblast and primitive endoderm stages. In addition, it is known that knock-out mice lacking the expression of Oct-3/4 do not have inner cell mass (ICM). Specifically, the direction of differentiation into different target cells is determined depending on the amount of Oct-3/4. Therefore, it is expected that the control of expression level of the Oct-3/4 protein makes it possible to prepare specific differentiated cells efficiently and abundantly. And, based on this, it will be possible to establish an efficient method for regulating proliferation and differentiation of cells through revealing the mechanism of proteolysis and to ultimately discover a large amount of therapeutic agents to be used for therapeutic purposes through differentiation.

DISCLOSURE

Technical Problem

The present inventors performed various studies including bioinformatics analysis in order to elucidate the mechanism for ubiquitination of the Oct-3/4 protein. As the results thereof, it has been found that the protein variants, in which the specific amino acid residues of the Oct-3/4 protein (i.e., lysines at positions 156 and 286 of the Oct-3/4 protein) were substituted with arginine, not only inhibit the proteolytic mechanism through ubiquitination but also show a high half-life, thereby exhibiting high stability. Accordingly, it is an object of the present invention to provide an Oct-3/4 protein variant.

Technical Solution

In accordance with an aspect of the present invention, there is provided an Oct-3/4 protein variant wherein lysine at position 156; lysine at position 286; or lysines at positions 156 and 286 in the Oct-3/4 protein consisting of the amino acid sequence of SEQ ID NO: 1 is (are) substituted with arginine.

In an embodiment, the Oct-3/4 protein variant may be a variant consisting of the amino acid sequence of SEQ ID NO: 3, 4, or 5.

Advantageous Effects

The Oct-3/4 protein variant according to the present invention can inhibit the proteolytic mechanism through ubiquitination; and shows a higher half-life, compared to the wild-type Oct-3/4, thereby exhibiting high stability. Therefore, the variant according to the present invention can effectively express Oct-3/4 and thus may be usefully used for the production of induced pluripotent stem cells. And, target cells in the direction required for treatment, such as neuron cells (an ectoderm differentiated from an embryonic body (EB)), cardiac muscles (a mesoderm differentiated from EB), and pancreatic cells (an endoderm differentiated from EB), can be specifically produced through inhibiting the degradation mechanism of the Oct-3/4 protein involved in the differentiation mechanism of cells. In addition, since the Oct-3/4 protein variant according to the present invention shows a high half-life, thereby exhibiting high stability, mass production thereof is possible. In addition, the Oct-3/4 protein variant according to the present invention can regulate proliferation and differentiation of cells, and thus be usefully used in the development of an agent for cell therapy. Oct-3/4 shows a high expression level in cancer cells. Although the E3 ligase acting on the Oct-3/4 variant has not yet been identified, the expression of Oct-3/4 protein regulated through the E3 ligase inhibits the proliferation of cancer cells and thus the Oct-3/4 protein variant could be also usefully applied for the cell therapy thereto.

BEST MODE

The present inventors performed bioinformatics analysis in order to find out the ubiquitination site of the Oct-3/4 protein and found that the lysine residues at specific sites, i.e., the lysine residues at position 128, 144, 156, and 286, may be related to ubiquitination of the Oct-3/4 protein. From said results, the Oct-3/4 variants (i.e., Oct-3/4 K128R, Oct-3/4 K144R, Oct-3/4 K156R, and Oct-3/4 K286R), in which lysine at position 128, 144, 156, or 286 is substituted with arginine respectively, were prepared. Among the variants, it was confirmed that ubiquitinations of the Oct-3/4 K156R and the Oct-3/4 K286R were significantly inhibited. And, it has been found that when the Oct-3/4 K156R and the Oct-3/4 K286R were treated with cycloheximide, a protein synthesis inhibitor, they showed a higher half-life, compared to the wild-type Oct-3/4, thereby exhibiting excellent stability. Therefore, the variant can effectively express Oct-3/4 and thus may be usefully used e.g., for the production of induced pluripotent stem cells. In addition, since the variant shows a high half-life, thereby exhibiting high stability, mass production thereof is possible.

The present invention provides a variant of the Oct-3/4 protein consisting of the amino acid sequence of SEQ ID NO: 1. That is, the present invention provides an Oct-3/4 protein variant wherein lysine at position 156; lysine at position 286; or lysines at positions 156 and 286 in the Oct-3/4 protein consisting of the amino acid sequence of SEQ ID NO: 1 is (are) substituted with arginine.

The amino acid sequence of the Oct-3/4 protein and the nucleotide sequence encoding the same are known in the art. For example, the NCBI accession number of the Oct-3/4 protein is NP_002692.2 (SEQ ID NO: 1) and the NCBI access number of the nucleotide sequence encoding the Oct-3/4 protein is NM_001285986.1 (SEQ ID NO: 2).

In an embodiment, the Oct-3/4 protein variant according to the present invention may be a variant in which lysine at position 156 in the Oct-3/4 protein consisting of the amino acid sequence of SEQ ID NO: 1 is substituted with arginine, i.e., the variant consisting of the amino acid sequence of SEQ ID NO: 3. In another embodiment, the Oct-3/4 protein variant according to the present invention may be a variant in which lysine at position 286 in the Oct-3/4 protein consisting of the amino acid sequence of SEQ ID NO: 1 is substituted with arginine, i.e., the variant consisting of the amino acid sequence of SEQ ID NO: 4. In still another embodiment, the Oct-3/4 protein variant according to the present invention may be a variant in which lysines at position 156 and 286 in the Oct-3/4 protein consisting of the amino acid sequence of SEQ ID NO: 1 are substituted with arginine, i.e., the variant consisting of the amino acid sequence of SEQ ID NO: 5.

The Oct-3/4 protein variant according to the present invention may be prepared by substituting lysine at position 156; lysine at position 286; or lysines at position 156 and 286 with arginine, according to a method conventionally used in the field of biotechnology. For example, using a gene encoding the Oct-3/4 protein (e.g., a gene having the nucleotide sequence of SEQ ID NO: 2) as a template, polymerase chain reactions may be carried out with the primer sets of SEQ ID NOs: 10 and 11 below, so as to obtain a variant in which lysine at position 156 is substituted with arginine. In addition, for example, using a gene encoding the Oct-3/4 protein (e.g., a gene having the nucleotide sequence of SEQ ID NO: 2) as a template, polymerase chain reactions may be carried out with the primer sets of SEQ ID NOs: 12 and 13 below, so as to obtain a variant in which lysine at position 286 is substituted with arginine.

As described above, the Oct-3/4 protein variant according to the present invention can inhibit the proteolytic mechanism through ubiquitination and thus may be usefully used e.g., for the production of induced pluripotent stem cells. In addition, since the Oct-3/4 protein variant according to the present invention shows a high half-life, thereby exhibiting high stability, mass production thereof is possible. Therefore, the Oct-3/4 protein variant according to the present invention can be applied to the development of effective agents for cell therapy and anticancer drugs.

Hereinafter, the present invention will be described more specifically by the following examples. However, the following examples are provided only for illustrations and thus the present invention is not limited to or by them.

EXAMPLES (1) Selection of Ubiquitination Sites and Preparation of Variants

Bioinformatics analysis was performed through the following nine websites (Table 1), so as to analyze the ubiquitination site candidates of the Oct-3/4 protein. As a result thereof, lysines at the positions 128, 144, 156, and 286 were found to be the most repetitive amino acid residues, i.e., the amino acid residues with the highest efficiency, and were used as ubiquitination site candidates.

TABLE 1

Ubiquitination Prediction Sites

<http://www.ubpred.org>
<http://csb.cse.yzu.edu.tw/UbiSite/>
<http://bdmpub.biocuckoo.org/prediction.php>
<http://202.195.183.4:8000/mUbiSiDa.php
(reprod.njmu.edu.cn/mUbiSiDa)>
<http://www.jci-bioinfo.cn/iUbiq-Lys>
<http://protein.bio.unipd.it/rubi/>
<http://csb.cse.yzu.edu.tw/UbiNet/>
<https://omictools.com/ubiquitination-sites-category>
<http://www.cbs.dtu.dk/services/NetChop/>

The Oct-3/4 variants (i.e., Oct-3/4 K128R, Oct-3/4 K144R, Oct-3/4 K156R, and Oct-3/4 K286R) were prepared by substituting lysine at the position 128, 144, 156, or 286 of the Oct-3/4 protein with arginine, using the primer sets shown in the following Table 2. Specifically, using the wild-type Oct-3/4 gene (the gene of SEQ ID NO: 2) as a template, polymerase chain reactions (PCRs) were performed with each primer set. The PCR (a total of 14 cycles) was performed under the conditions of: 3 minutes at 95° C. for denaturation, 1 minute at 56° C. for annealing, and 12 minutes at 68° C. for extension. After carrying out electrophoresis on an agarose gel, the bands amplified by each primer were identified through Gel Doc.

TABLE 2

| Variant | SEQ ID NO | | Sequence |
|---|---|---|---|
| Oct-3/4 K128R | 6 | Forward | GAG AAG GAG AGG CTG GAG CAA |
| | 7 | Reverse | TTG CTC CAG CCT CTC CTT CTC |
| Oct-3/4 K144R | 8 | Forward | GCT CTG CAG AGA GAA CTC GAG |
| | 9 | Reverse | CTC GAG TTC TCT CTG CAG AGC |
| Oct-3/4 K156R | 10 | Forward | CTG AAG CAG AGG AGG ATC ACC |

TABLE 2-continued

| Variant | SEQ ID NO | | Sequence |
|---|---|---|---|
| | 11 | Reverse | GGT GAT CCT CCT CTG CTT CAG |
| Oct-3/4 K286R | 12 | Forward | CAG AAG GGC AGG CGA TCA AGC |
| | 13 | Reverse | GCT TGA TCG CCT GCC CTT CTG |

The nucleotide sequences of the obtained variants, i.e., Oct-3/4 K128R, Oct-3/4 K144R, Oct-3/4 K156R, and Oct-3/4 K286R, were analyzed, with the primers (ATT TAG GTG ACA CTA TAG) designated for the plasmids thereof, using the 3730xl Analyzer (Applied Biosystems, USA). As a result thereof, it was confirmed that lysines at positions 128, 144, 156, and 286 of Oct-3/4 were respectively substituted with arginine.

(2) Expression Analysis by Western Blotting

Figure 1:
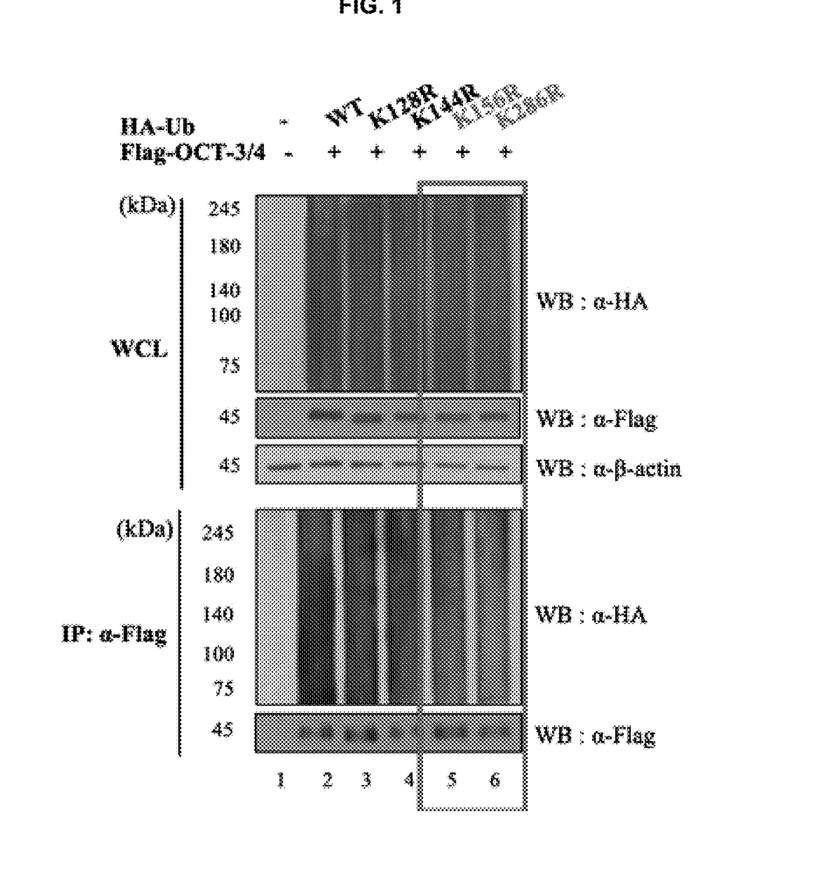
FIG. 1 shows the results of Western blotting (upper panel) and the results of immunoprecipitation with the Flag antibody (lower panel), after the HA-labeled ubiquitination enzyme and the Flag-labeled wild-type Oct-3/4 or Flag-labeled Oct-3/4 variants (i.e., Oct-3/4 K128R, Oct-3/4 K144R, Oct-3/4 K156R, or Oct-3/4 K286R) were transfected into 293T cells.

The HA-labeled ubiquitination enzyme and the Flag-labeled wild-type Oct-3/4 or Flag-labeled Oct-3/4 variants (i.e., Oct-3/4 K128R, Oct-3/4 K144R, Oct-3/4 K156R, or Oct-3/4 K286R) were transfected into 293T cells, followed by Western blotting. The results thereof are as shown in FIG. 1 (upper panel in FIG. 1). In addition, immunoprecipitation was performed using the Flag antibody, and the results thereof are shown in FIG. 1 (lower panel in FIG. 1). From the results of FIG. 1, it can be confirmed that ubiquitinations of the Oct-3/4 K156R and the Oct-3/4 K286R were significantly inhibited.

Figure 2:
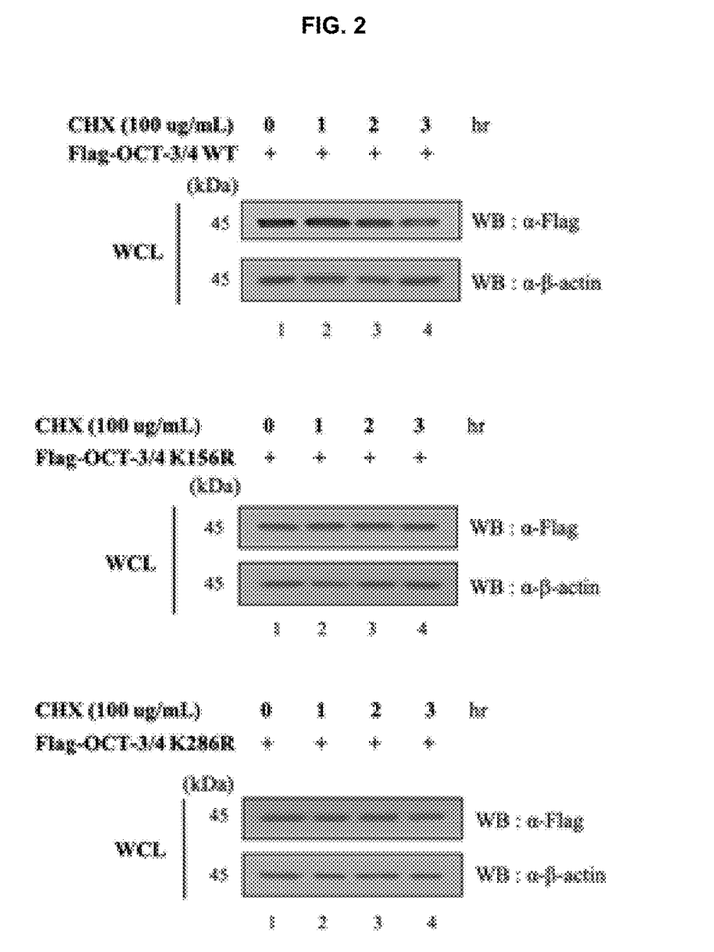
FIG. 2 shows the results obtained by measuring the expression levels of Oct-3/4 from 0 to 3 hours at 1 hour intervals through Western blotting, after respectively transfecting the wild-type Oct-3/4, Oct-3/4 K156R, and Oct-3/4 K286R into 293T cells and then treating with cycloheximide (CHX), a protein synthesis inhibitor.
Figure 3:
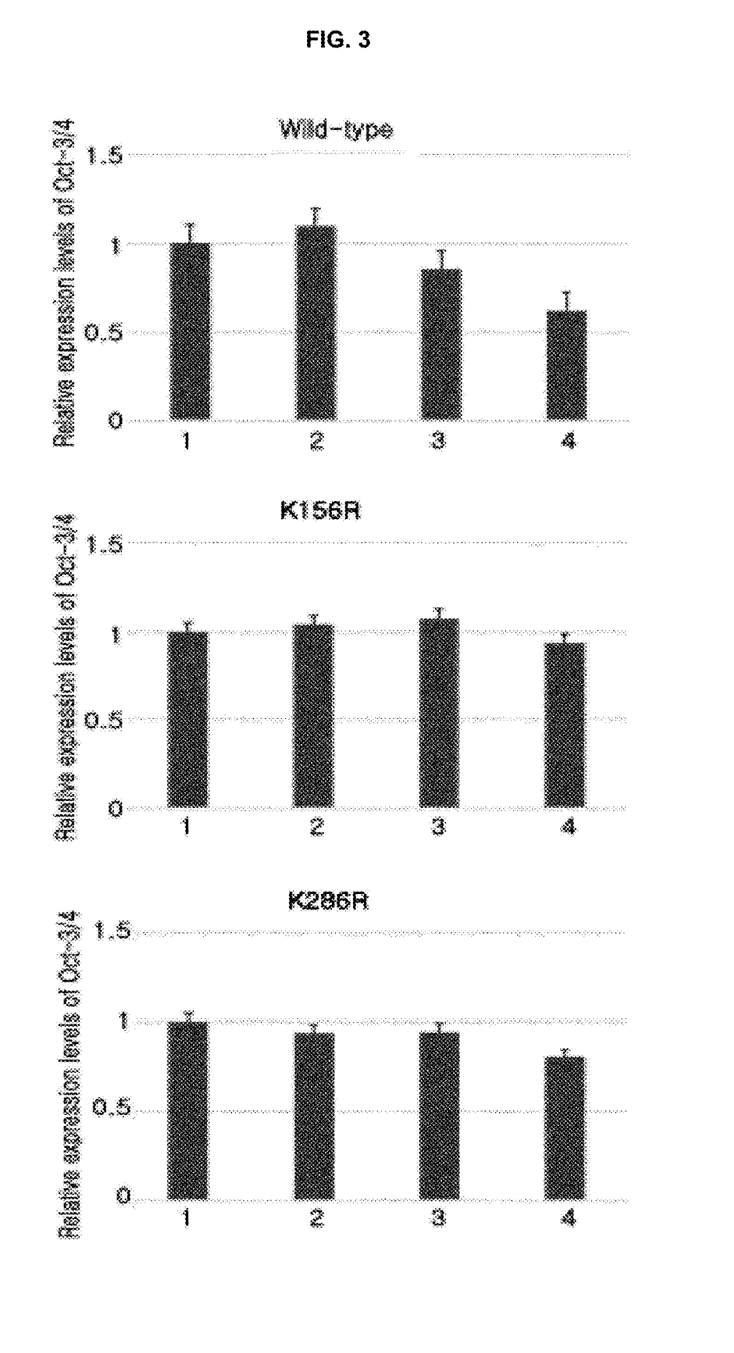
FIG. 3 shows the results obtained by calculating the relative Oct-3/4 expression levels from 0 to 3 hours from the results of FIG. 2.

(3) Analysis of Oct-3/4 Expression According to Treating Protein Synthesis Inhibitor The wild-type Oct-3/4, Oct-3/4 K156R, and Oct-3/4 K286R were respectively transfected into 293T cells and then treated with cycloheximide, a protein synthesis inhibitor. The expression levels of Oct-3/4 from 0 to 3 hours at 1 hour intervals were measured through Western blotting, and the results thereof are shown in FIG. 2. In addition, the results of calculating the relative Oct-3/4 expression levels from 0 to 3 hours from the results of FIG. 2 are shown in FIG. 3. As can be seen from the results of FIGS. 2 and 3, when viewed as 1 based on 0 hour, the expression of the wild-type Oct-3/4 was decreased to 0.62 at 3 hours after the treatment with cycloheximide; however, the Oct-3/4 K156R was decreased to 0.94 and Oct-3/4 K286R was decreased to 0.8, indicating a higher half-life than the wild-type Oct-3/4. Therefore, it can be confirmed that the Oct-3/4 K156R and the Oct-3/4 K286R have a longer half-life.

The invention claimed is:

1. An octamer-binding transcription factor 3/4 (OCT-3/4) protein variant wherein lysine at position 286; or lysines at positions 156 and 286 in the Oct-3/4 protein consisting of the amino acid sequence of SEQ ID NO: 1 is (are) substituted with arginine.

2. The Oct-3/4 protein variant according to claim 1, consisting of the amino acid sequence of SEQ ID NO: 4.

3. The Oct-3/4 protein variant according to claim 1, consisting of the amino acid sequence of SEQ ID NO: 5.

* * * * *